United States Patent [19]
Prugh

[11] 4,089,864
[45] May 16, 1978

[54] 4-(10,11-DIHYDRO-CIS AND TRANS-10,11-DIHYDROXY-5H-DIBENZO[a,d]CYCLOHEPTEN-5-YLIDENE)-PIPERIDINES

[75] Inventor: John D. Prugh, Chalfont, Pa.

[73] Assignee: Merck & Co., Inc., Rahway, N.J.

[21] Appl. No.: 454,195

[22] Filed: Mar. 25, 1974

[51] Int. Cl.$^2$ .......................... C07D 211/22
[52] U.S. Cl. ............................... 260/293.62
[58] Field of Search ...................... 260/293.62

[56] References Cited

U.S. PATENT DOCUMENTS

| | | | |
|---|---|---|---|
| 3,014,911 | 12/1961 | Engelhardt | 260/293 |
| 3,234,279 | 2/1966 | Kollonitsch et al. | 260/570.8 |
| 3,352,869 | 11/1967 | Engelhardt | 260/293 |
| 3,642,808 | 2/1972 | Schroter et al. | 260/293.62 |
| 3,660,389 | 5/1972 | Hucker et al. | 260/247.2 |

OTHER PUBLICATIONS

Shirley, "Organic Chemistry", Holt, Rinehart and Winston, New York (1964), pp. 198–199.

Primary Examiner—Henry R. Jiles
Assistant Examiner—Richard A. Schwartz
Attorney, Agent, or Firm—Harry E. Westlake, Jr.; Nicholson, William H.

[57] ABSTRACT

10,11-dihydroxy derivatives of 10,11-dihydro cyproheptadine useful as appetite enhancers and as antihistaminic agents are prepared from a process including bromination and alkaline hydrolysis of the resulting 10,11-dibromo compounds.

5 Claims, No Drawings

4-(10,11-DIHYDRO-CIS AND TRANS-10, 11-DIHYDROXY-5H-DIBENZO[a,d]CYCLOHEPTEN-5-YLIDENE)-PIPERIDINES

SUMMARY

This invention concerns 10,11-dihydroxy-10,11-dihydro-5H-dibenzo[a,d]cyclohepten-5-ylidene piperidine compounds, acid addition salts thereof, and processes for the preparation of said compounds from the corresponding 5H-dibenzo[a,d]cycloheptene-5-ylidene piperidine compounds. It also concerns pharmaceutical compositions in which said 10,11-dihydroxy compounds are incorporated as the active medicinal agent. The invention is also concerned with the use of such compounds in the treatment of certain allergic conditions including those caused by excess histamine including seasonal rhinitis, hay fever, dermatitis and the use of such compounds as appetite stimulants.

BACKGROUND

A variety of drugs have been used in the past to aid as antihistaminic agents or as appetite stimulants, including those characterized as 1-alkyl-4-(5H-dibenzo[a,d]cyclohepten-5-yliden)-piperidines and the 10-keto or 10-hydroxy derivatives thereof.

Prior to the present invention, it was known that the compound cyproheptadine of the structure

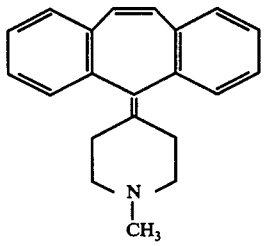

and the 10-keto or 10-hydroxy derivative were active antihistaminic and/or antiserotonin agents and were therefore useful in the treatment or relief of certain allergic conditions. This is disclosed in U.S. Pat. No. 3,014,911, Edward L. Engelhardt, which patent was issued Dec. 26, 1961, and in John D. Prugh Canadian Pat. No. 912,553, which was issued Oct. 17, 1972.

The 10-oxo or -hydroxy compounds of the prior art are also known to possess enhanced antihistaminic activity and appetite stimulant properties relative to the 10-unsubstituted compounds. This is disclosed in Canadian Pat. No. 912,553 mentioned above.

DESCRIPTION AND PREFERRED EMBODIMENTS

The present invention relates to 10,11-dihydroxy derivatives of 4-(10,11-dihydro-5H-dibenzo[a,d]cyclohepten-5-ylidene)-piperidine which are useful because of their ability to enhance appetite in undernourished patients or in patients with low appetite and as antihistaminic agents useful in the treatment of allergic conditions including seasonal rhinitis, hay fever, and dermatitis. In particular, it relates to derivatives of the following structure:

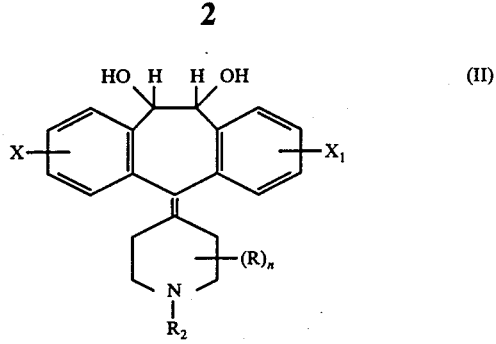

wherein
$R_2$ is hydrogen, loweralkyl, or loweralkenyl, preferably containing from 1 to 6 carbon atoms;
X and $X_1$ are similar or dissimilar and are selected from hydrogen,
  an alkyl group having up to 6 carbon atoms,
  a phenyl or a substituted phenyl radical,
  an acyl group having up to 4 carbon atoms,
  a perfluoroacyl group having up to 4 carbon atoms,
  amino,
  an alkylamino group having up to 4 carbon atoms,
  a dialkylamino group having up to 8 carbon atoms,
  an acylamino group having up to 4 carbon atoms,
  a perfluoroacylamino group having up to 4 carbon atoms,
  an alkysulfonylamino group having up to 4 carbon atoms,
  halogen (fluorine, chlorine, bromine, or iodine),
  hydroxyl,
  an alkoxyl group having up to 4 carbon atoms,
  a perfluoroalkoxyl group having up to 4 carbon atoms,
  cyano,
  carboxy,
  carbamoyl,
  formyl,
  an alkylcarbamoyl group having up to 5 carbon atoms,
  a dialkylcarbamoyl group having up to 9 atoms,
  a carbalkoxy group having up to 6 carbon atoms,
  an alkylmercapto group having up to 4 carbon atoms,
  an alkylmercapto group, especially benzylmercapto,
  a perfluoroalkylmercapto group having up to 4 carbon atoms,
  an alkylsulfonyl group having up to 4 carbon atoms,
  a perfluoroalkylsulfonyl group having up to 4 carbon atoms,
  sulfamoyl,
  an alkylsulfamoyl group having up to 4 carbon atoms,
  a dialkylsulfamoyl group having up to 8 carbon atoms,
  or an alkylsulfinyl group having up to 4 carbon atoms;
R is methyl or ethyl and may replace one or more of the hydrogens in positions 2, 3, 5 or 6 of the pyridine ring, provided that only one of positions 3 or 5 is monosubstituted at one time; and
n is 1 or 2.

The invention also includes non-toxic pharmaceutically acceptable salts of the above compounds such as acid addition salts which may interchangeably be used in therapeutic applications with the base and likewise includes N-oxide derivatives thereof.

The salts are formed in solution by reaction of the base with a pharmaceutically acceptable non-toxic acid such as hydrochloric, hydrobromic, nitric, lactic, citric, tartaric, maleic, fumaric and the like.

The invention also includes the administration of a 4-(10,11-dihydro-10,11-dihydroxy-5H-dibenzo[a,d]cyclohepten-5-ylidene)-piperidine or an acid addition salt as antihistaminic agents to combat the effect of excess histamine or to treat specific allergic conditions such as seasonal rhinitis, hay fever, and dermatitis. The treatment involves preferably the oral administration of an effective amount of the selected 10,11-dihydroxy-10,11-dihydro-dibenzo[a,d]cyclohepten-5-ylidene)-piperidine at a dosage level which will combat the effect of excess histamine or relieve the specific allergic condition being treated.

The invention also includes a method of stimulating appetite in human patients who may be underweight or malnourished. The method employed for stimulating appetite involves the administration either orally or parenterally, but preferably orally, of an effective amount of a selected 4-(10,11-dihydro-10,11-dihydroxydibenzo[a,d]-cyclohepten-5-ylidene)-piperidine.

The compounds of the present invention may be administered to undernourished persons, persons with low appetite, or persons suffering from excess histamine in the blood stream or from specific allergic conditions such as seasonal rhinitis, hay fever or dermatitis, in any of the usual pharmaceutical oral forms such as tablets, elixirs and aqueous suspensions in an amount of from 1.0 up to 500 mgs. per dose given 2 to 4 times daily. Sterile solutions for injection containing from 0.1 to about 250 mgs. per dose are injected 2 to 4 times a day. Further, the compounds of this invention are ordinarily easily administered as a salt and any convenient non-toxic acid addition salt formed in a conventional manner may be employed. In accordance with the process of my invention, liquid pharmaceutical formulations are prepared by dissolving or suspending the active compound or salt in water. For preparing the solid dosage forms such as tablets or capsules the active ingredient is mixed with a pharmaceutical diluent or excipient and/or binding agent such as lactose, magnesium stearate, corn starch, or mixtures thereof. The formulation mixture is then sub-divided in accordance with methods known in the art to provide unit dosage forms which will provide the doses recommended hereinabove. As examples of the salts convenient for use are salts of the compounds of the present invention with hydrochloric acid, hydrobromic acid, sulfuric acid, nitric acid, phosphoric acid, acetic acid, propionic acid, lactic acid, citric acid, tartaric acid, fumaric acid, succinic acid, maleic acid and the like. These salts are generally equivalent in potency to the bases from which they are formed taking into consideration the stoichiometric quantities employed.

The compounds of the present invention are conveniently prepared from the compounds disclosed in the Prugh Canadian Pat. No. 912,553, issued Oct. 17, 1972, said compounds being either a 1-alkyl-4-(5H)-dibenzo[a,d]cyclohepten-5-ylidene)-piperidine or appropriately substituted derivatives thereof. These starting materials set forth in the Prugh patent are prepared in accordance with the process of that patent, particularly the process described at pages 6 through 22 of the patent. The process disclosed involves treating a 4-(5H-dibenzo[a,d]cyclohepten-5-ylidene)-piperidine or the 1-alkyl derivative thereof in the form of its hydrobromide salt with bromine to produce the corresponding 4-(10,11-dibromo-10,11-dihydro-5H-dibenzo[a,d]-cyclohepten-5-ylidene)-piperidine.

In accordance with the process of the present invention, the starting material, i.e., the 4-(10,11-dibromo-10,11-dihydro-5H-dibenzo[a,d]cyclohepten-5-ylidene)-piperidine (I) is treated in an inert polar solvent with hydroxide ion, but preferably by dissolving the salt in water, to produce the biologically active 10,11-dihydroxy derivative of 4-(10,11-dihydro-5H-dibenzo[a,d]-cyclohepten-5-ylidene)-piperidine (II). The product produced in this manner is biologically active and is a mixture of primarily the cis and trans isomers, the major portion being present in the cis configuration. The cis isomer of the compound may be isolated by selective fractional crystallization.

The trans isomer with a small amount of cis isomer and other products remains in the crystallization mother liquors. The trans isomer is then isolated from the crystallization mother liquors by column chromatography using an absorbent such as silica gel. In a typical isolation, the mixture of the cis-trans isomers is absorbed on a column of treated silica gel and eluted with chloroform saturated with aqueous ammonia. The cis isomer is generally eluted just prior to the trans isomer. The separated products are then isolated from the appropriate fractions. In those cases where the cis isomer fails to separate by crystallization, the crude reaction product as the free base is chromatographed directly.

The corresponding N-alkenyl compounds, for example the N-allyl compound, may be prepared from the free base by reaction with an equivalent amount of allyl bromide in the presence of a base to produce, for example, 1-allyl-4-(10,11-dihydro-10,11-dihydroxy-5H-dibenzo[a,d]cyclohepten-5-ylidene)-piperidine.

The process of preparing the compounds of the present invention is illustrated in the following reaction flow sheet:

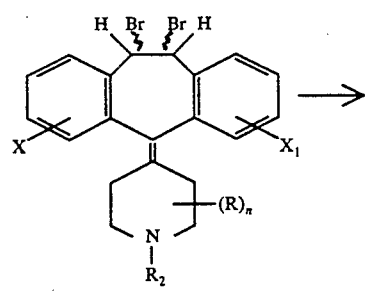

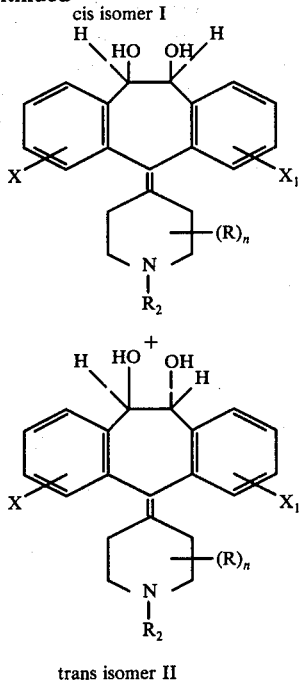

cis isomer I trans isomer II wherein R, $R_2$, X, $X_1$ and n are as defined hereinabove.

It will be apparent to one skilled in the art that the compounds of the present invention, which are unsymmetrically substituted, are usually obtained as a mixture of isomers. These isomers, i.e., the geometrical, stereo and/or the optical isomers, are separated at any desired stage of the process. In addition, the mixtures of isomers formed are readily subjected to the various processing steps with consequent production of a mixture of isomers of the final product which in turn are readily separated by known means. The isomers of the product of the present invention when isolated in their pure form differ in biological activity.

The process outlined in the above flowsheet is a method of introducing 10,11-dihydroxy substituents into compound I, i.e., 4-(10,11-dibromo-10,11-dihydro-(5H-dibenzo[a,d]cyclohepten-5-ylidene)-piperidine or the corresponding 1-alkyl derivative by the process of hydrolysis. This process is also applicable to the derivatives indicated in which the benzene rings are substituted by one or more of the named substituents.

EXAMPLE 1

1-Methyl-4-(10,11-dihydro-cis-10,11-dihydroxy-5H-dibenzo[a,d]cyclohepten-5-ylidene)-piperidine, I 1-Methyl-4-(10,11-dihydro-10,11-dibromo-5H-dibenzo[a,d]cyclohepten-5-ylidene)-piperidine hydrobromide (Canadian Pat. No. 912,553), 71.7 g. (0.136 mole) is dissolved in 5 l. of degassed distilled water and stirred overnight under nitrogen. The reaction is divided into half. The first half is made basic with sodium bicarbonate and shaken with approximately 1 l. of ether. A crystalline material, crude I, separates and is collected. The water is extracted four times with 500 ml. portions of ether. The combined ether extracts are dried over anhydrous magnesium sulfate, filtered, and all but approximately 100 ml. of the ether evaporated. More crude I crystallizes, is collected, washed with ether, and combined with the first crop to give a total of 5.1 g. of crude I. The ether filtrate is evaporated to leave an oil, called A. Approximately 100 ml. of ether is added to the other half of the reaction. It is then made basic with sodium hydroxide solution (pH approximately 12) and shaken. The granular precipitate is filtered and washed with water and ether to give another 9.6 g. of crude I. The aqueous layer is extracted with three approximately 100 ml. portions of ether. The filtrate and ether washings are combined, dried over anhydrous magnesium sulfate, filtered, and the solvent evaporated to leave an oil called B. The strongly basic aqueous layer is called C. The portions of I are combined and recrystallized from ethanol to give 11.60 g. of 1-methyl-4-(10,11-dihydro-cis-10,11-dihydroxy-5H-dibenzo[a,d]cyclohepten-5-ylidene)-piperidine, m.p. 246°–255° C. (D). The solvent from the mother liquor is evaporated leaving an oil called D. An analytical sample from an additional recrystallization melted at 248°–255° C., $R_f$ 0.63 Fl-silica developed with 5% methanol in chloroform saturated with ammonia and water.

Calc. for $C_{21}H_{23}NO_2$: C, 78.47; H, 7.21; N, 4.36. Found: C, 78.36; H, 7.28; N, 4.00.

Proton magnetic resonance absorption of I ($d_6$-DMSO): $\delta$ 1.9–2.8 (M, 11, $C_4H_8NCH_3$, peak 2.14, $\underline{CH_3}$) 5.07 (S, 4, —C$\underline{H}$O$\underline{H}$C$\underline{H}$O$\underline{H}$—) 6.9–7.6 (M, 8H, aromatic); change after adding $D_2O$, 3.48 (S, 2, O$\underline{H}$) 5.07 (S,2—C$\underline{H}$OHC$\underline{H}$OH—).

EXAMPLE 2

1-Methyl-4-(10,11-dihydro-trans-10,11-dihydroxy-5H-dibenzo[a,d]-cyclohepten-5-ylidene)-piperidine, II All of the oils containing II, oils A, B and D from Step A are combined and chromatographed twice on 400 g. each of silica gel (70–230 mesh ASTM) which had been previously stirred for 1 hour with chloroform saturated with ammonia and water (CAW) 1.5 l., and the product eluted with chloroform saturated with ammonia and water. The desired product, II, emerges from the column after traces of the cis-isomer. The $R_f$ of the desired product, II, is 0.41 Fl-silica developed with 5% methanol in CAW. The solvent is removed from the fractions containing only II and the oil taken up in ether and extracted with 10% sodium hydroxide. The ether solution is dried over magnesium sulfate, filtered and most of the ether evaporated. The desired product, 1-methyl-4-(10,11-dihydro-trans-10,11-dihydroxy-5H-dibenzo[a,d]cyclohepten-5-ylidene)-piperidine, II, 3.68 g., is crystallized from the small remaining amount of ether, m.p. 233°–237° C. (D) after drying.

Calc. for $C_{21}H_{23}NO_2$: C, 78.47; H, 7.21; N, 4.36. Found: C, 78.65; H, 7.42; N, 4.32.

Pmr of II ($d_6$-DMSO): $\delta$ 1.9–2.9 (M, 11, $C_4H_8NCH_3$, peak 2.18-$\underline{CH_3}$), 4.36 (d, 1, $J_{ab}$ = 9Hz, —C$\underline{H}$OH), 5.26 (d, 1, $J_{ab}$=9Hz, —C$\underline{H}$OH), 5.60 (S, 2, —CHOHC$\underline{H}$O$\underline{H}$), 6.8–7.8 (M, 8, aromatic).

EXAMPLE 3

9,10-Dihydro-10-(1-methyl-4-piperidylidene)-9-anthraldehyde, III (Method 1)

The strongly basic water layer C from Step A with no time lapse is filtered and very carefully concentrated hydrochloric acid is added until the solution is only slightly basic (approximately pH 9). A white precipitate forms which is extracted with dichloromethane. The solvent is evaporated to give a solid, which upon recrystallization from acetonitrile gives 0.5 g. of 9,10-dihydro-10-(1-methyl-4-piperidylidene-9-anthraldehyde, III, 159.5°–160.5° C.

Calc. for $C_{21}H_{21}NO$: 83.13; H, 6.98; N, 4.62. Found: 82.80; H, 6.89; N, 4.49.

Pmr DCCl$_3$: δ1.7–3.2 (M, 11, C$_4$H$_8$NC$\underline{H}_3$, peak 2.22, C$\underline{H}_3$) 4.61 (d, 0.6,

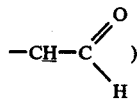

7.0–7.6 (M, 8, aromatic) 8.3–9.0 (M, 0.8 – other conformer of

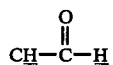

or C=C$\underline{H}$O$\underline{H}$), 9.5 (d, 0.6

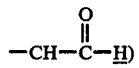

EXAMPLE 4

9,10-Dihydro-10-(1-methyl-4-piperidylidene)-9-anthraldehyde, III (Method 2)

1-Methyl-4-(10,11-dihydro-cis-10,11-dihydroxy-5H-dibenzo[a,d]cyclohepten-5-ylidene)-piperidine, 3.21 g., is dissolved in 500 ml. of 1 N HCl and heated in an oil bath at 100° C. for 90 minutes. The reaction is cooled in an ice bath and 200 ml. of ether added. Sodium bicarbonate is added until no more bubbles are formed, and the product is extracted with three 100 ml. portions of ether. The combined ether extracts are dried over anhydrous sodium sulfate, filtered, and evaporated. The remaining solid is triturated with approximately 20 ml. of ether and the pale yellow solid collected and dried to give 2.07 g., m.p. 157°–160° C. This product, the same as that prepared (as indicated by I.R.) from Method 1, changes form on prolonged heating with acetonitrite and an insoluble form crystallizes, weight 1.1 g., m.p. 207°–210° C.

Calc. for $C_{21}H_{21}NO$: C, 83.13; H, 6.98; N, 4.62. Found: C, 83.06; H, 7.16; N, 4.72.

Pmr in d$_6$-DMSO: δ1.6–3.1 (M, 11, C$_4$H$_8$NCH$_3$, peak 2.08, CH$_3$) 6.9–8.5 (8 aromatic plus 1 vinyl) 8.8 (broad S, 1, O$\underline{H}$) change on adding D$_2$O 4.12 (S, 1, OH) No peak at 8.8 therefore product primarily in the enol form in d$_6$-DMSO.

Pmr in DCCl$_3$ similar to that reported under Method 1.

EXAMPLE 5

4-(10,11-Dihydro-cis-10,11-dihydroxy-5H-dibenzo[a,d]-cyclohepten-5-ylidene)-piperidine, I; and
4-(10,11-Dihydro-trans-10,11-dihydroxy-5H-dibenzo[a,d]cyclohepten-5-ylidene-piperidine, II A. 4-(5H-Dibenzo[a,d]cyclohepten-5-ylidene)-piperidine hydrobromide (Salt formate)

5H-Dibenzo[a,d]cyclohepten-5-ylidene piperidine (1) (9.2 g., 33.7 mmoles) is dissolved in 150 ml. of benzene. Ether (150 ml.) is added and dry hydrogen bromide bubbled in with stirring until no more precipitate is formed. The salt is filtered, washed with ether, and dried in a vacuum oven overnight at 80° C. giving 11.84 g. of 4-(5H-dibenzo[a,d]-cyclohepten-5-ylidene)-piperidine hydrobromide, m.p. 311°–313° C. (D).

(1) E. L. Engelhardt et al., *J. Med. Chem.* 8, 829 (1965)

B. 4-(10,11-Dibromo-10,11-dihydro-5H-dibenzo[a,d]cyclohepten-5-ylidene)-piperidine hydrobromide 4-(5H-dibenzo[a,d]cyclohepten-5-ylidene)-piperidine hydrobromide (3.45 g., 10 mmoles) is dissolved in 500 ml. of acetic acid at 100° C., the solution allowed to cool with stirring to 70° C. and bromine (1.60 g., 10 mmoles) dissolved in 30 ml. of acetic acid is added dropwise over a period of 30 minutes. The reaction is then stirred for 2 hours at room temperature. The product which crystallizes from the reaction is collected, washed four times with ether with stirring to get rid of as much acetic acid as possible. The washed product is quickly placed in a vacuum oven at 50° C. and dried for 30 minutes giving 4.90 g. of 4-(10,11-dibromo-10,11-dihydro-5H-dibenzo[a,d]cyclohepten-5-ylidene)-piperidine hydrobromide, m.p. 194°–195° C. (D). This material is used directly in the next step.

C. 4-(10,11-Dihydro-10,11-cis-dihydroxy-5H-dibenzo[a,d]cyclohepten-5-ylidene)-piperidine, I 4-(10,11-dibromo-10,11-dihydro-5H-dibenzo[a,d]cyclohepten-5-ylidene)-piperidine hydrobromide (11.26 g., 21.9 mmoles) slowly dissolves over a period of approximately 4.5 hours when stirred at room temperature in 2 l. of distilled degassed water under nitrogen. At least 200 ml. of a 10% sodium hydroxide solution is added and shaken with ether.

A product crystallizes, is collected, and is washed with ether. This material is recrystallized from absolute ethanol to give 0.85 g. of 4-(10,11-dihydro-10,11-cis-dihydroxy-5H-dibenzo[a,d]-cyclohepten-5-ylidene)-piperidine, m.p. 242°–248° C. (D). R$_f$ = 0.70 Fl-silica developed with 15% methanol in CAW.

Calc. for $C_{20}H_{21}NO_2$: C, 78.15; H, 6.89; N, 4.56. Found: C, 78.02; H, 6.88; N, 4.57.

Pmr, DCCl$_3$: δ 2.30 (T, 4, J= 6Hz, 2CH$_2$ of C$_4$H$_9$N) 2.56–3.08 (M, 4, 2C$\underline{H}_2$, of C$_4$H$_9$N), 5.29 (S, 2, —C$\underline{H}$OH-C$\underline{H}$OH—), 7.04–7.25 (M, 6, aromatic) 7.24–7.39 (M, 2, aromatic).

D. 4-(10,11-Dihydro-10,11-trans-dihydroxy-5H-dibenzo[a,d]cyclohepten-5-ylidene)-piperidine, II The basic aqueous phase from the ether extraction of Step C is further extracted 5 times with 100 ml. portions of dichloromethane. These extracts are combined with the ether extract of Step C, dried over anhydrous sodium sulfate, filtered and the solvent removed leaving a semi-solid which is chromatographed on 350 g. of silica gel pretreated with chloroform saturated with ammonia and water (CAW). The product is eluted with CAW with an increasing amount of methanol in 5% increments to 10%. The desired product II is eluted after the change to 10% methanol in CAW and emerges after the cis-diol product I. The fractions containing the desired product II are combined, the solvent evaporated, the product taken up in ether, washed with dilute sodium hydroxide solution, dried over anhydrous magnesium sulfate, filtered, and all but approximately 3 ml. of solvent evaporated. This gives 0.33 g. of 4-(10,11-dihydro-10,11-trans-dihydroxy-5H-dibenzo[a,d]cyclohepten-5-ylidene)-piperidine, II, m.p. 210°–226° C. (D). Two recrystallizations from absolute ethanol gives an analytical sample, m.p. 226°–230° C. (D).

Calc. for $C_{20}H_{21}NO_2$: 78.15; H, 6.89; N, 4.56. Found: 78.09; H, 6.98; N, 4.54.

Pmr DCCl₃: δ 2.33 (T, 2, J=6Hz, CH₂ of C₄H₉N) 2.50 (T, 2, J=6Hz, CH₂ of C₄H₉N); 2.60–3.08 (M, 4, 2CH₂ of C₄H₉N); 4.53 (d, 1, J_{ab} = 10Hz —CHOHCHOH—); 5.37 (d, 1, J_{ab} = 10 Hz —CHOHCHOH—) 6.78–7.25 (M, 6, aromatic) 7.32–7.68 (M, 2, aromatic).

What is claimed is:

1. The compound of structural formula:

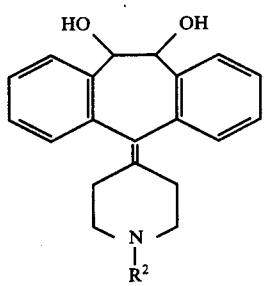

wherein R₂ is hydrogen, or lower alkyl, having from 1 to 6 carbon atoms.

2. 1-Methyl-4-(10,11-dihydro-cis-10,11-dihydroxy-5H-dibenzo[a,d]cyclohepten-5-ylidene)-piperidine.

3. 1-Methyl-4-(10,11-dihydro-trans-10,11-dihydroxy-5H-dibenzo[a,d]cyclohepten-5-ylidene)-piperidine.

4. 4-(10,11-Dihydro-10,11-cis-dihydroxy-5H-dibenzo[a,d]cyclohepten-5-ylidene)-piperidine.

5. 4-(10,11-Dihydro-10,11-trans-dihydroxy-5H-dibenzo[a,d]cyclohepten-5-ylidene)-piperidine.

* * * * *